US008783871B2

(12) United States Patent
Pamplona et al.

(10) Patent No.: US 8,783,871 B2
(45) Date of Patent: Jul. 22, 2014

(54) NEAR EYE TOOL FOR REFRACTIVE ASSESSMENT

(75) Inventors: Vitor Pamplona, Somerville, MA (US); Manuel Menezes de Oliveira Neto, Porto Alegre (BR); Ankit Mohan, San Mateo, CA (US); Ramesh Raskar, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 33 days.

(21) Appl. No.: 13/577,880

(22) PCT Filed: Apr. 22, 2011

(86) PCT No.: PCT/US2011/033681
§ 371 (c)(1),
(2), (4) Date: Sep. 20, 2012

(87) PCT Pub. No.: WO2011/133945
PCT Pub. Date: Oct. 27, 2011

(65) Prior Publication Data
US 2013/0027668 A1    Jan. 31, 2013

Related U.S. Application Data

(60) Provisional application No. 61/327,083, filed on Apr. 22, 2010.

(51) Int. Cl.
*A61B 3/02* (2006.01)
*A61B 3/00* (2006.01)

(52) U.S. Cl.
USPC ............ 351/239; 351/236; 351/246; 351/211

(58) Field of Classification Search
CPC ..................................... A61B 3/02; A61B 3/00
USPC ......... 351/205, 208, 209, 216, 236, 239, 243, 351/246
See application file for complete search history.

(56) References Cited

U.S. PATENT DOCUMENTS

| | | | | |
|---|---|---|---|---|
| 7,290,880 B1 * | 11/2007 | Yaron et al. | ................... | 351/206 |
| 7,475,989 B2 * | 1/2009 | Campbell et al. | ............. | 351/246 |
| 8,016,420 B2 * | 9/2011 | Yee et al. | ....................... | 351/211 |
| 8,520,060 B2 * | 8/2013 | Zomet et al. | .................... | 348/51 |

* cited by examiner

*Primary Examiner* — Loha Ben
(74) *Attorney, Agent, or Firm* — Stephen R. Otis

(57) ABSTRACT

In exemplary implementations, this invention is a tool for subjective assessment of the visual acuity of a human eye. A microlens or pinhole array is placed over a high-resolution display. The eye is brought very near to the device. Patterns are displayed on the screen under some of the lenslets or pinholes. Using interactive software, a user causes the patterns that the eye sees to appear to be aligned. The software allows the user to move the apparent position of the patterns. This apparent motion is achieved by pre-warping the position and angle of the ray-bundles exiting the lenslet display. As the user aligns the apparent position of the patterns, the amount of pre-warping varies. The amount of pre-warping required in order for the user to see what appears to be a single, aligned pattern indicates the lens aberration of the eye.

39 Claims, 14 Drawing Sheets

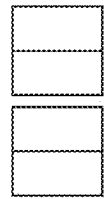
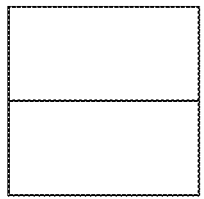
FIG. 8A
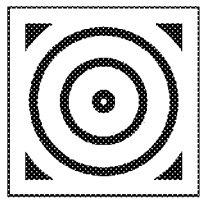
FIG. 8B
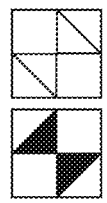
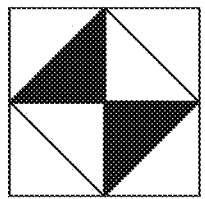
FIG. 8C
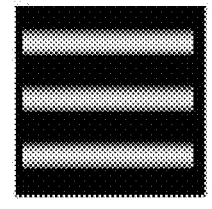
FIG. 8D
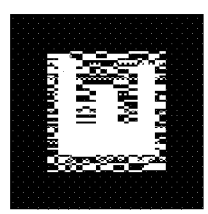
FIG. 8E

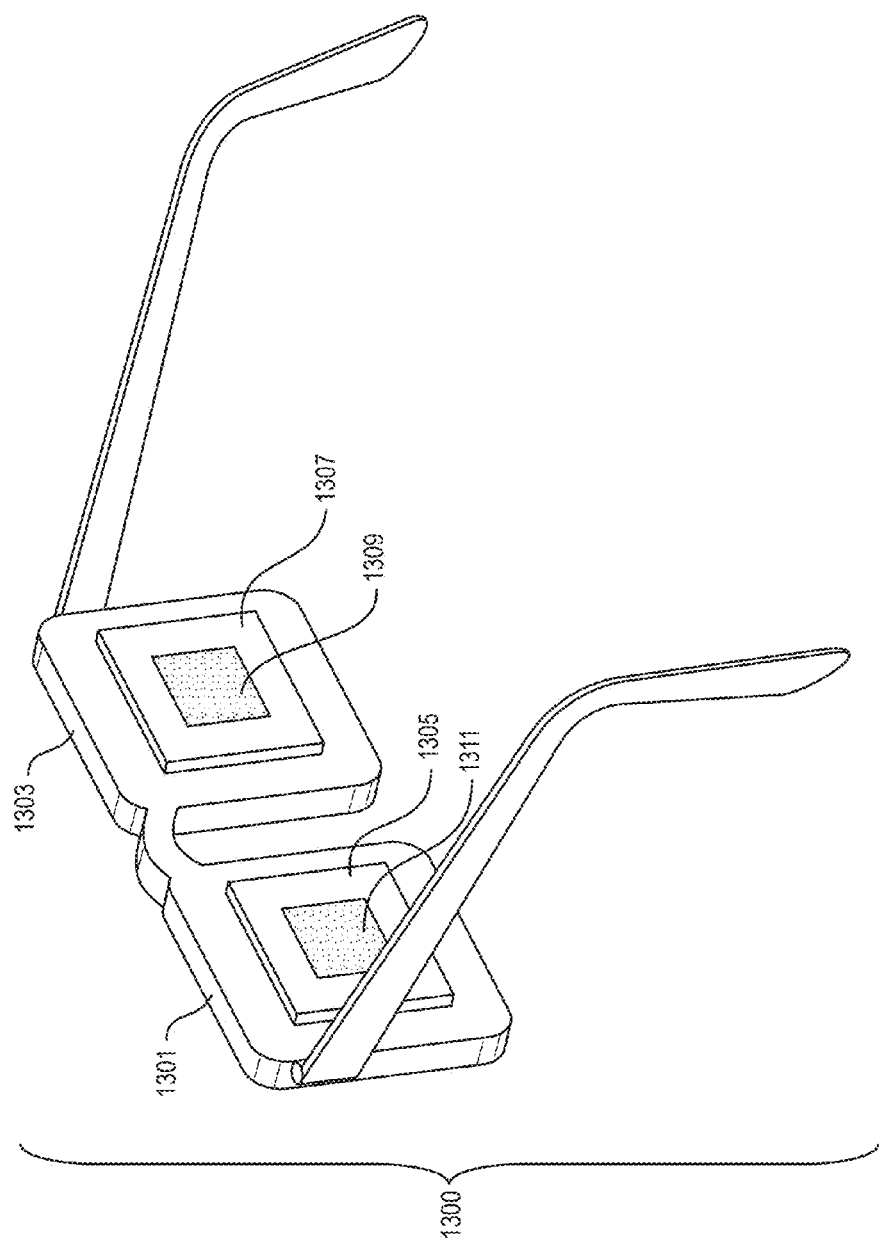

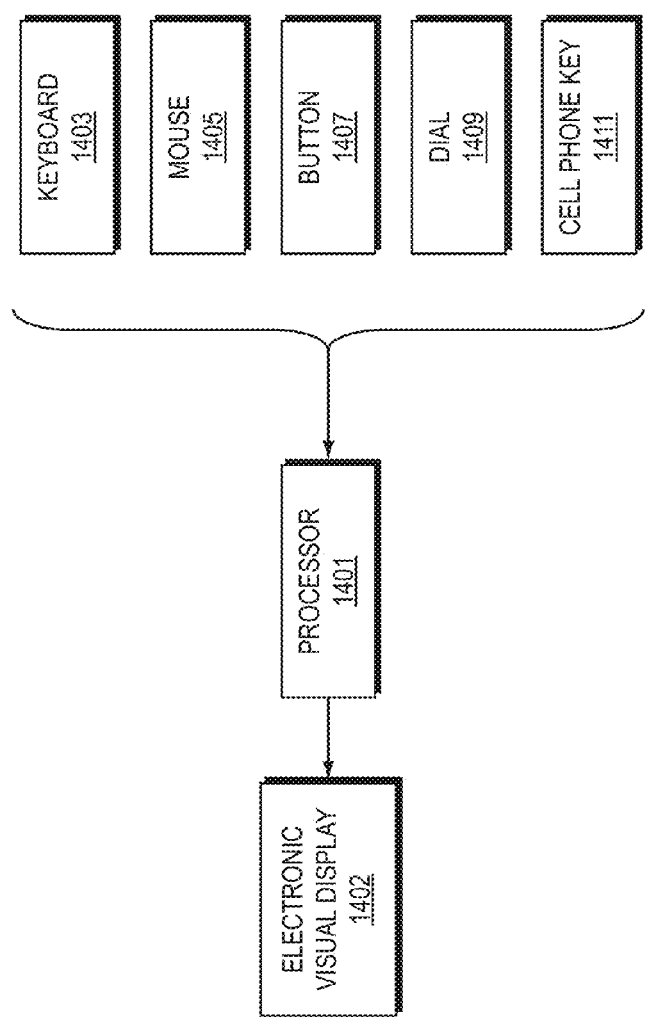

NEAR EYE TOOL FOR REFRACTIVE ASSESSMENT

RELATED APPLICATIONS

This application claims the benefit of U.S. Provisional Application Ser. No. 61/327,083, filed Apr. 22, 2010, the entire disclosure of which is herein incorporated by reference.

FIELD OF THE TECHNOLOGY

The present invention relates generally to optometers and the assessment of refractive disorders.

BACKGROUND

Refractive disorders of the eye include myopia (bad far sight), hyperopia (bad near sight), astigmatism, and presbyopia. In myopia, the eye can focus at shorter distances (e.g., less than 30 cm to less than infinity), but cannot focus at infinity. In hyperopia, the eye can focus at or past infinity, but cannot focus at some shorter distances (e.g., at 30 cm). When the crystalline lens is completely relaxed: (a) a perfect eye focuses parallel rays to a single point on the retina; (b) an eye with myopia focuses parallel rays to a point before the retina; and (c) an eye with hyperopia focuses parallel rays to a point after the retina.

Astigmatism is a refractive condition caused by a toric curvature in the cornea or in the crystalline lens. In this case the eye has different curvatures along two perpendicular meridians; thus, it cannot sharply focus an image on the retina. Put differently, an astigmatic eye refracts light in a radially asymmetric manner.

Accommodation is the adjustment of the shape of the eye's crystalline lens, in order to focus on an object. During accommodation, the shape of the lens changes from more planar (when the eye is focusing at a far scene) to more spherical (when focusing on a near object).

Presbyopia is a reduction in the eye's ability to perform accommodation experienced by most individuals starting at the age of 40. As such, it is considered a natural stage of the eye's aging process.

Refractive correction for myopia, hyperopia, and astigmatism can be achieved with the use of corrective lenses. The refractive power of a lens is expressed in diopters, a unit defined as the reciprocal of the lens' focal length expressed in meters. A diverging lens (negative diopters) may be used to correct myopia. A converging lens (positive diopters) may be used to correct hyperopia.

Refractive eye disorders are the 2nd leading cause of blindness worldwide. [World Health Organization, Visual impairment and blindness, Factsheet, 2010] Over 153 million people around the world suffer from uncorrected refractive vision problems and 87% of them—133.11 million people—reside in developing nations. [B. Holden, Uncorrected refractive error: the major and most easily avoidable cause of vision loss, Community Eye Health, Vol. 20(63), pp. 37-39, 2007] Many of these sufferers do not have access to appropriate diagnostic and treatment options due to cost—they live on less than a dollar a day—and due to an insufficient number of optometrists. Lots of them do not even know that the vision difficulties or headaches are due to refractive errors. For many children, hyperopia is not diagnosed since they can see objects clearly. However, because they are putting extra effort to focus at infinity, over time it added stress and headache. All these problems lead to a tremendous loss in productivity in the developing countries, with estimated losses ranging from USD 88.74 to USD 133 billion.

It would be highly desirable to have a low cost, accurate tool for assessing refractive disorders, particularly for use in some developing countries, where optometrists are in short supply or patients cannot afford an optometrist. It would be very helpful if such a tool could be used for screening and diagnosis, and to determine the spherical power, cylindrical power and cylindrical axis of the eyeglass prescription needed to correct the refractive disorder.

SUMMARY

In exemplary implementations of this invention, these goals can be achieved.

In exemplary implementations, this invention is a tool for subjective assessment of the visual acuity of a human eye. A microlens or pinhole array is placed over a high-resolution display. The eye is brought very near the device. Patterns are displayed on the screen under some of the lenslets or pinholes. Using interactive software, the user causes the patterns that the eye sees to appear to be aligned (to overlap). The software allows the user to move the apparent position of the patterns. This apparent motion is achieved by pre-warping the position and angle of the ray-bundles exiting the lenslets or pinholes. As the user aligns the apparent position of the patterns, the amount of pre-warping varies. The amount of pre-warping required in order for the user to see what appears to be a single, aligned pattern indicates the lens aberration of the eye.

This is different from conventional methods of assessing refractive disorders, in which blur as an indicator of misfocus. It can be difficult, in conventional methods, for a viewer to determine if one image is more blurred than another. In exemplary embodiments of this invention, the problem of alignment replaces blur estimation. It is easy for a user to tell if two images are becoming more aligned (e.g., if two lines are moving closer to each other).

For an eye that has radially symmetric vision (i.e., is not astigmatic) and does not have higher-order aberrations, a simple one step method may be used to assess the degree of myopia or hyperopia, in exemplary embodiments of this invention. The LCD displays a pattern. The user employs interactive software to change the virtual distance of that pattern (farther from or closer to the lenslet). For example, the LCD could initially display the pattern at a virtual distance at which the eye can sharply focus. The user could increase the virtual distance until he begins to see multiple, overlapping images, and then could decrease the virtual distance until he sees only a single image again. By doing so, the far focus distance may be determined. From the far focus distance, the degree of myopia or hyperopia, as the case may be, can be determined. (For a myopic eye, the far focus distance is less than infinity; for a hyperopic eye, it is greater than infinity). The far focus distance will be equal to 1/S, where S is the spherical power of the eyeglass prescription.

If the eye being tested is astigmatic, however, this one step method will not work. In astigmatism, the eye refracts light in a radially asymmetric manner. As a result, the user will not be able to align the patterns into a sharp, single image.

To solve this problem, in exemplary implementations of this invention, a two-step method may be used to assess an eye that is or may be astigmatic.

In the first of these two steps, parameters of an eyeglass prescription (the eye's spherical power, cylindrical power and cylindrical axis) may be easily determined from a small number of measurements along different meridians. For example, in the first measurement, two lenslets with an angle of θ may be employed. ("With an angle of θ" means that the line that intersects the center of the two lenslets has an angle θ with respect to some reference). Under each of the two lenslets, the LCD displays a line with an orientation (π+θ). Using interactive software, the user moves the apparent position of the two displayed lines in 1D (closer or farther apart from each other). The two lines will appear to the user to be aligned when the distance from the lenslet to the virtual object is equal to $1/(S+C\sin^2(\alpha-\theta))$, where S is the eye's spherical power, C is its cylindrical power, and α is the angle of the cylindrical axis. The measurements are repeated along different meridians, where $\theta \in [0,\pi)$. For example, the measurements may be repeated up to eight times along equally spaced meridians. However, the number of samples may be more or less than eight, and the meridians do not need to be equally spaced. These samples are used to find an optimal (in the least squares sense) estimate of the eye's parameters.

These measurements indicate whether the eye is myopic, hyperopic or astigmatic. From the spherical power (S), it can be determined whether the eye is myopic or hyperopic. From the cylindrical power and cylindrical axis (C and α), one can determine whether and how the eye is astigmatic.

In the second of these two steps, the user's range of accommodation can also be determined. A user's "range of accommodation" means the range of distances at which an uncorrected eye may sharply focus on an object. The maximum of the range is the far focus distance (the farthest distance at which the uncorrected eye can sharply focus); and the minimum of the range is the short focus distance (the shortest distance at which the uncorrected eye can sharply focus).

In this second step of the two-step method, symmetric projections along the cylindrical axis may be used to determine the user's range of accommodation, as follows: (If the first step shows that the eye does not have astigmatism—i.e., if the eye has radially symmetric vision—then any cylindrical axis may be used). The LCD displays a 1D sinusoidal pattern to the eye being tested. The user employs interactive software to change the virtual distance of that sinusoidal pattern (farther from or closer to the lenslet). When the virtual distance is within the eye's range of accommodation, the user sees only a single, unchanging image of the sinusoid. However, when the virtual distance goes outside the range of accommodation (further than the far focus distance or shorter than the short focus distance), the user sees multiple (and in some cases, partially overlapping) images of the sinusoid. In this manner, the far focus distance and short focus distance (and thus the range of accommodation) can be determined.

During these tests, the optimal focus varies. Sometimes, it is desirable for the eye to focus at infinity (for measuring myopia, hyperopia and astigmatism). At other times, it is desirable for the eye to focus at the virtual distance (for measuring presbyopia). For example, in the first step of the two-step method described above (when testing for astigmatism), it is desirable for the eye to focus at infinity. In contrast, in second step of the two-step method described above (when testing for range of accommodation in an astigmatic eye), it is desirable for the eye to focus at the virtual distance.

The light rays from each lenslet, respectively, are collimated. This cue tends to cause the eye to tend to focus at infinity. A straight line does not overpower this cue. Thus, it is preferable to use a straight line for those measurements in which focus at infinity is desired (such as the first step of the two-step method described above). In contrast, a sinusoidal shape forces the eye to focus at the virtual distance. Thus, it is preferable to use a sinusoidal shape for those tests in which focus at the virtual distance is desired (such as the second step of the two-step method described above).

In exemplary implementations, the speed of accommodation of an optical system may also be assessed. For example, an image may be displayed at one virtual depth in one frame, and at another virtual depth in the next frame. The speed at which the optical system accommodates to the new depth may be measured using software.

In exemplary implementations with an LCD display screen and lenslet array, there are no physically moving optical elements. For example, no pinhole or mirror changes its physical position. Instead, the images displayed on the LCD screen changes.

Nor, in those exemplary inventions, is a virtual light source created within the eye. For example, no laser light is shone into the eye to create a virtual light source inside the eye, in order to take measurements of light as it exits the eye (as is done in the conventional Shack-Hartmann technique).

The display screen may be housed in a variety of form factors. For example, it may comprise a display screen of a cell phone, smart phone, or head mounted display (HMD). Or, for example, the display screen may comprise a computer monitor. In that case, relay optics may be used to create, at the focal plane of the lenslet array, a minified display of the image on the computer monitor. In the same way, any kind of electronic visual display can be used. This system does not require LCDs. It can work with DMDs-based, DLPs-based, OLED, Plasma, CRT displays among others.

In some implementations, a regular array of pinholes may be used, rather than a lenslet array. The pinholes have less light throughput than a lenslet array. To compensate, a brighter display may be employed.

If a lenslet array is used, crosstalk between the ray bundles exiting from the respective lenslets may be reduced by skipping every other lenslet.

If pinholes are used, crosstalk between the ray bundles from the respective pinholes is also a problem, particularly when the space between pinholes is reduced (to increase light throughput) or the mask-to-pinhole distance is increased (to increase power resolution).

To solve that problem, jittered pinholes may be used. "Jittered" means that the pinholes are displaced randomly from a regular grid pattern. With a jittered pinhole pattern, the crosstalk (noise) appears as a blur to the viewer. When the displayed object is at a virtual distance at which the eye cannot sharply focus, the user sees only a blur. By scaling the drawings on the screen, the user may vary the virtual distance (e.g., by using interactive software to change an LCD display). When the virtual distance comes within the eye's range of accommodation, the object appears, standing out against the visual blur created by the crosstalk.

Another problem with pinholes is that the eye's focus tends to float. To solve this problem, when it is desirable that the eye being tested should focus at infinity, the user may be instructed to look at a distant scene with the other eye.

Another way to solve this problem (of the focal distance of the eye floating when pinholes are employed), is to use a beamsplitter to display two images at the same time to the eye being tested. The first image is a background image; the second is a test image with patterns that the viewer tries to align. The test image is created by a pinhole array. To the user, the test image appears to be located in the middle of the background image. The background image is a visual cue that tends to make the eye focus at the apparent distance of the background image, while the eye's visual acuity is being assessed using the test image.

The above description of the present invention is just a summary. It is intended only to give a general introduction to some illustrative implementations of this invention. It does not describe all of the details of this invention. This invention may be implemented in many other ways.

BRIEF DESCRIPTION OF THE DRAWINGS

FIGS. 8A, 8B, 8C, 8D and 8E each show, on the top, separate images displayed by an LCD screen, and on the bottom, how these appear as a single, aligned image to the viewer when the distance to the virtual point is within the eye's range of accommodation.

FIG. 13 is a diagram of lenslet arrays placed over the display screens of a head mounted display.

FIG. 15 lists examples of input devices that may be employed by the user in connection with this invention.

The above Figures illustrate some illustrative implementations of this invention, or provide information that relates to those implementations. However, this invention may be implemented in many other ways. The above Figures do not show all of the details of this invention.

DETAILED DESCRIPTION

Figure 1:
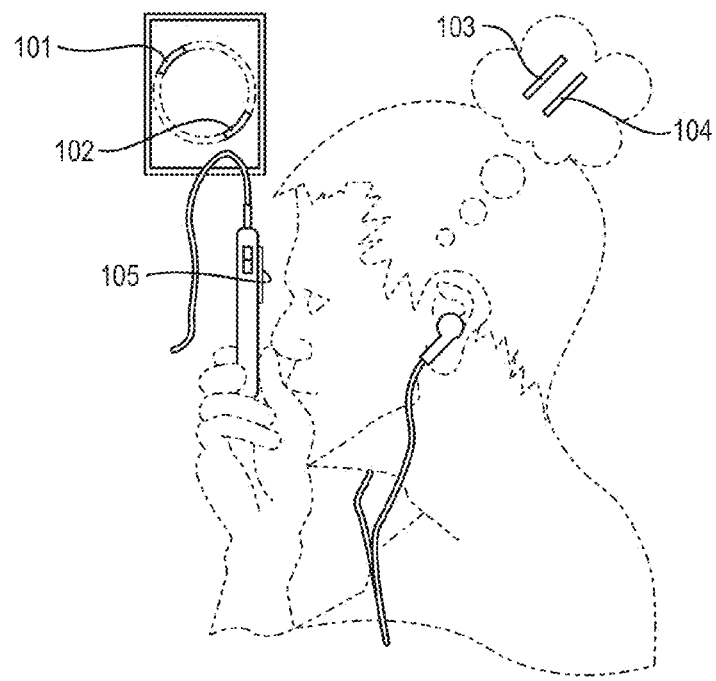
FIG. 1 shows a user viewing a cell phone screen at close range, in order to test visual acuity.

FIG. 1 shows a user holding a smartphone up to one of his eyes, in an exemplary implementation of this invention. The LCD display of the smartphone is covered by a microlens array 105. The LCD displays one green line 101 and one red line 102. The position of the lines so displayed is pre-warped to correct (at least partially) for the lens aberration of the eye. To the user, lines 101 and 102 appear as green line 104 and red line 103, respectively.

Figure 2:
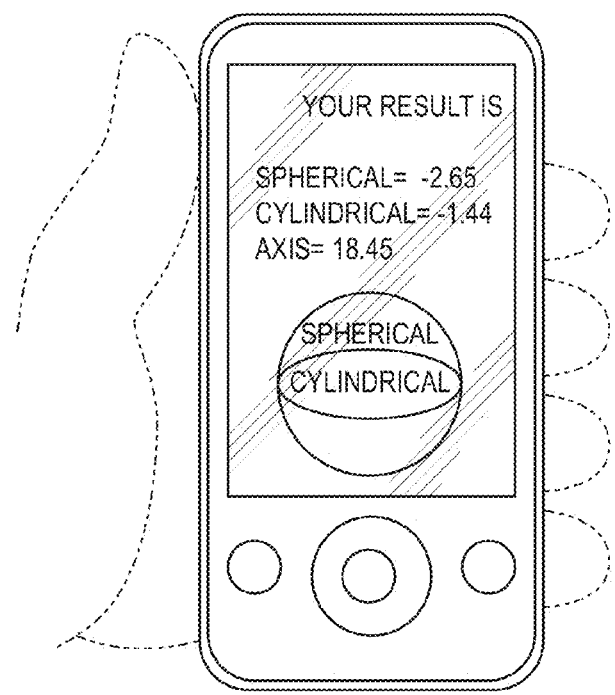
FIG. 2 shows a cell phone screen displaying the results of an assessment of the refractive power of an eye.

FIG. 2 shows a smartphone screen displaying the results of an assessment of visual acuity, in an exemplary implementation of this invention. The results displayed are standard parameters for an eyeglass prescription, namely (from top to bottom of the display) the spherical power, cylindrical power, and cylindrical axis. Other results may be displayed. For example, the screen may also display results for presbyopia, such as "Presbyopia: +3.00".

Figure 3:
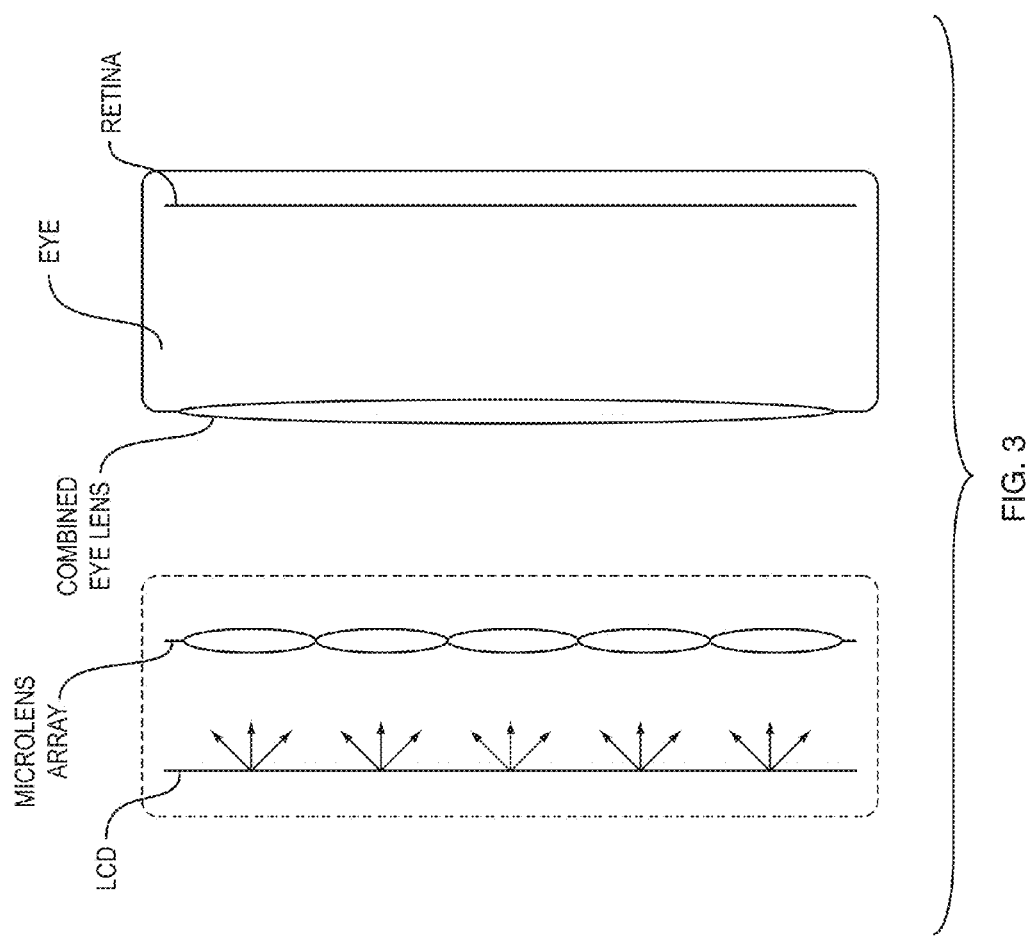
FIG. 3 is a diagram showing an LCD covered by a lenslet array.

FIG. 3 is a diagram showing a microlens array placed over a controllable high-resolution display screen, in an exemplary implementation of this invention. For example, the display screen may comprise an LCD screen. The viewer holds this setup next to the eye being tested. The image formed on the viewer's retina depends on the refractive properties of the tested eye. Using a simple interaction scheme, the user modifies the displayed pattern until the perceived image closely matches a specified result. Based on this interaction, the viewer's refractive conditions, such as myopia, hyperopia, and astigmatism, may be estimated. In FIG. 3 (and FIGS. 4 and 5 as well), for simplicity's sake, a single lens represents the combined refractive power of the cornea and the crystalline.

Figure 4:
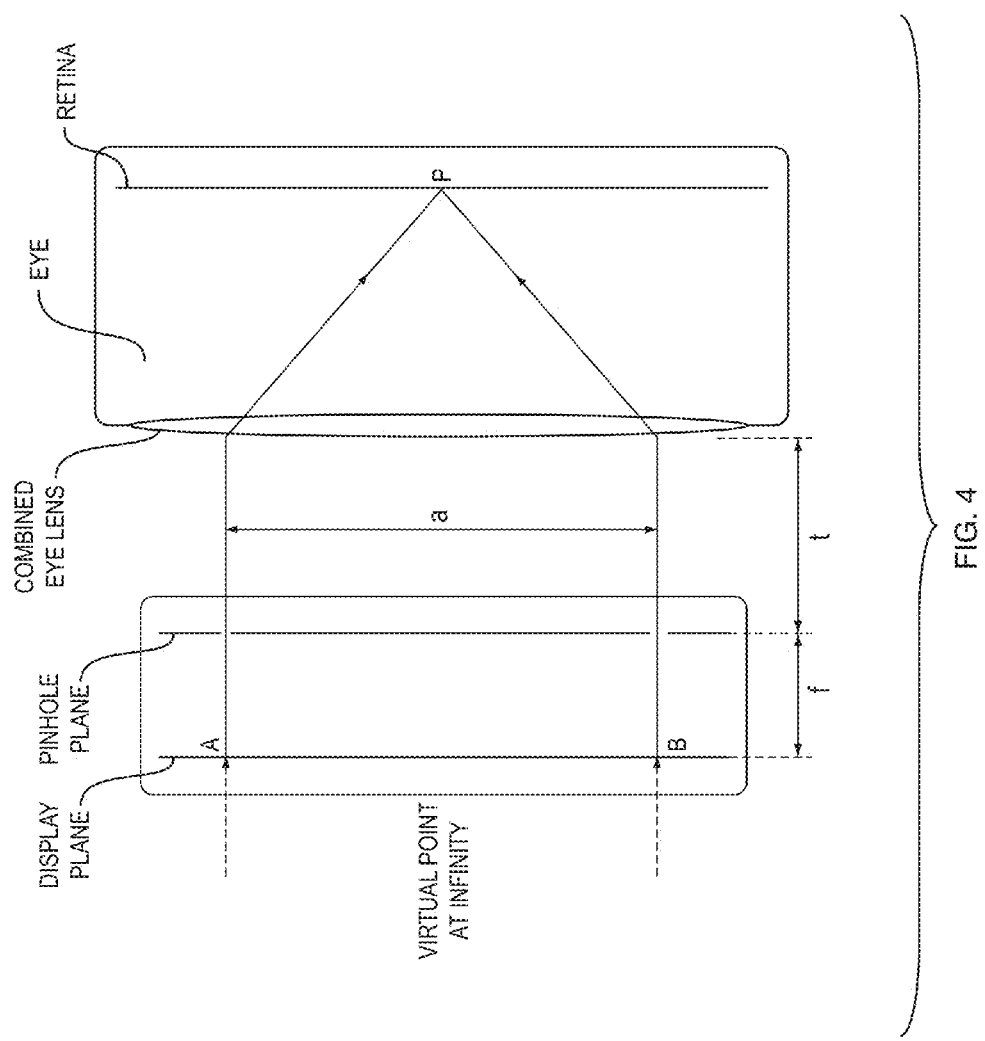
FIG. 4 is a diagram showing two parallel light rays from a virtual point at infinity passing through a pinhole array and being focused to a single point on the retinal plane.

In exemplary implementations of this invention, a pinhole array is placed over a controllable high-resolution LCD display. The array consists of eight pinholes, arrayed in a 3×3 regular grid. FIG. 4 is a simplified ray diagram for such a setup, showing two pinholes in flatland. As points directly under each pinhole (points A and B) are illuminated, two parallel rays enter the eye simulating a virtual point at infinity. An eye that can focus at infinity converges these rays, which meet at a single spot P on the retina.

Figure 5:
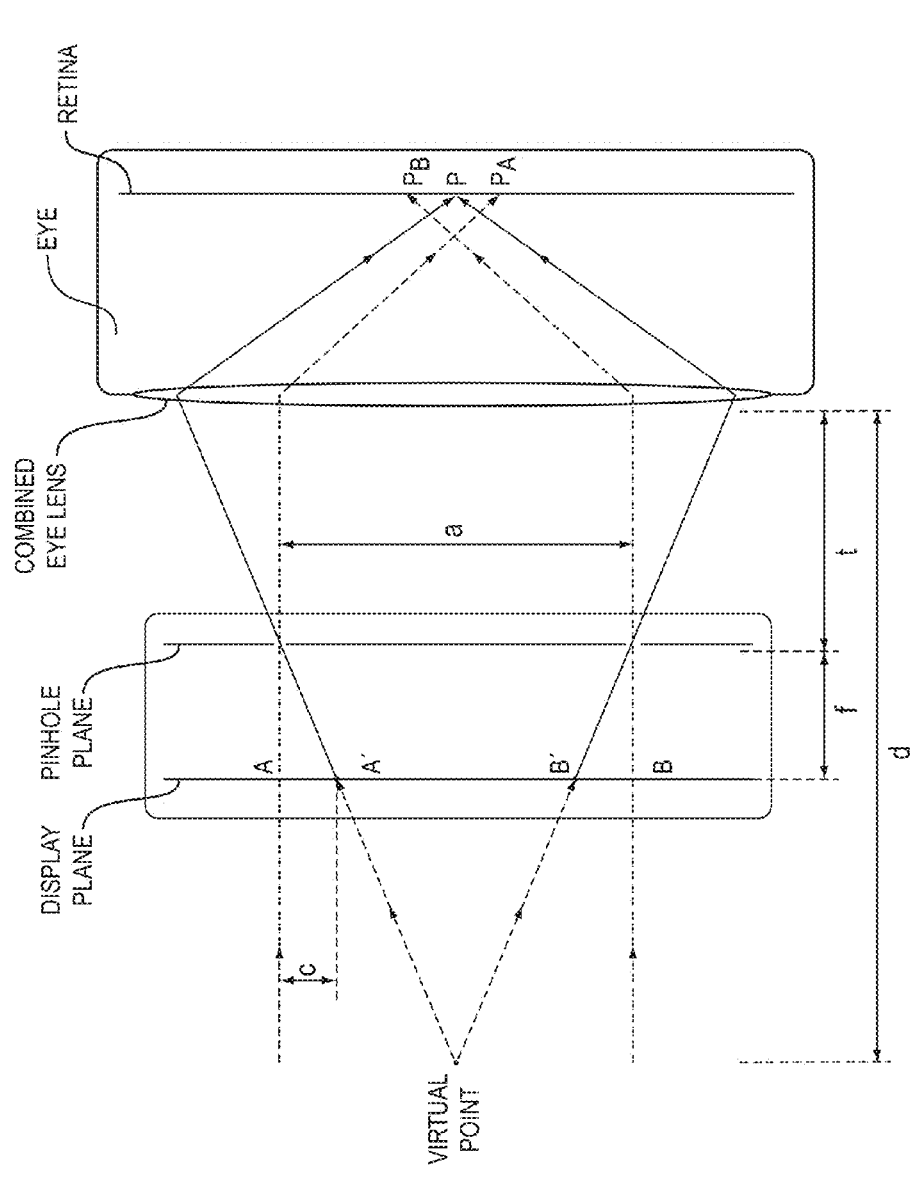
FIG. 5 shows light from a virtual point being focused by a myopic eye at different points on the retinal plane, depending on the distance to a virtual point.
Figure 6:
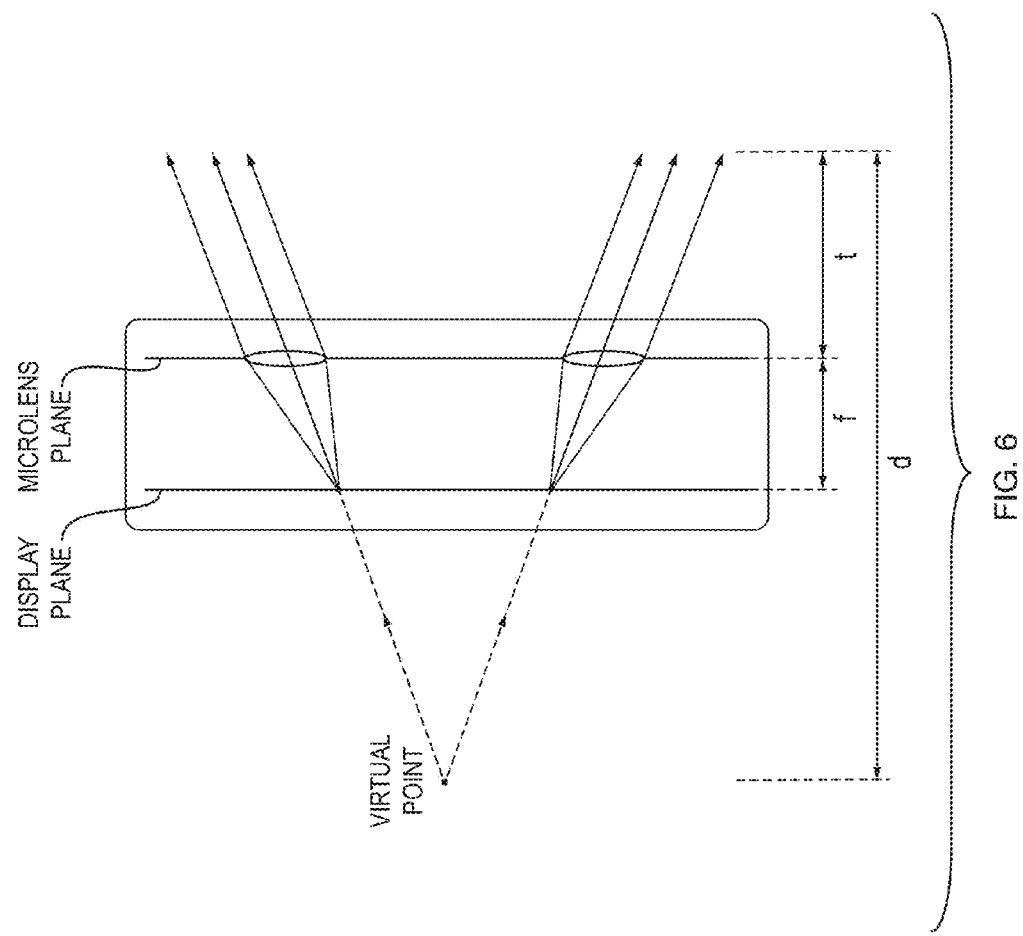
FIG. 6 shows light being collimated as it passes through the respective lenslets of a microlens plane.

FIG. 5 shows the same setup (display screen with pinhole array) as FIG. 4. However, in FIG. 5, the eye is myopic rather than perfect. As a result, parallel rays of light A and B are converged by the myopic eye to a single point in front of retina and then diverge again to strike the retina at points $P_A$ and $P_B$, respectively.

As shown in FIG. 5, changing the position of point A (or B) changes the vergence of the rays produced by the pinholes. For instance, moving points A and B closer to each other on the display plane, causes the corresponding rays to diverge, progressively moving the virtual point closer to the viewer. Likewise, moving these points apart causes the associated rays to converge, moving the virtual point away from the observer. For a myopic eye, as points A and B move closer, the two imaged spots overlap on the retina at P. The amount of shift applied to A and B indicates the refractive error in the viewer's eye. The case for hyperopia (bad near-sight) is similar: as points A and B are moved further apart on the display plane, the resulting rays converge, creating a virtual point "beyond infinity".

The amount of shift c required to create a virtual source at a distance d from the eye is:

$$c = (f/a)/(d-t) \quad \text{(Equation 1)}$$

where t is the distance from the pinhole array to the eye, a is the spacing between the pinholes, and f is the distance between the pinhole array and the display plane. (To the extent that the distances a, c, f, and t are shown in FIGS. 4 and 5, they have the same meaning as defined in the previous sentence.) Using a programmable LCD, the distance between the virtual scene point and the eye may be varied without any moving optical elements. This is equivalent to varying the power of a lens placed in front of the eye.

From Equation 1, the power of a diverging lens required to fix myopia is given (in diopters) by $D=(1/d)=1000/(f(a/2)/c+t)$, where all distances are in mm. Positive values for c and D represent myopia, while negative values represent hyperopia. If the eye-lenslet distance t is very small in comparison to the eye-virtual source distance, d, then for practical purposes t can be ignored for 5 diopters (d=200 mm) or below. In this case, the power of the diverging lens can be approximated as D=2000 c/fa. Correction for hyperopia can be computed in a similar way.

Unlike a real point, the virtual point projects a discontinuous set of rays into the eye. The number of rays arriving from the virtual point is limited to the number of pinholes. This produces a discontinuous circle of confusion for a point that is out of focus. In the case of two pinholes, we obtain two points on the retina (rather than a continuous circle of confusion) when the virtual point is out of focus. This difference allows us to convert a blur estimation problem into an easier alignment problem.

FIG. 5 shows a simplified ray diagram in flatland for a microlens array placed over an LCD screen, in an exemplary implementation of this invention. The lenslets permit greater light throughput than pinholes. In this lens-based setup, the microlens array is placed at a distance (from the LCD display screen) equal to the focal length of the microlenses. Instead of a single ray coming from each pinhole in one direction, we get a bundle of parallel rays, as shown in FIG. 5. This introduces a focus ambiguity: the eye can focus (or accommodate) either at the virtual point at a distance d, or at infinity to focus the parallel bundle of rays on the retina. As discussed below, one focus cue can be made stronger than the other by varying the displayed patterns.

The pupil size limits the maximum spacing between lenslets, which affects the achievable range of corrective power. Also, the granularity of the microlens array affects the resolution for the cylindrical axis (in the case of astigmatism).

The diopter resolution of our setup is limited by the size of the cone cells of the eye (effectively the pixel size of the retina), $p_e \sim 4$ μm, and eye's focal length, $f_e \sim 17$ mm. We assume that the human user can resolve misalignments of a single pixel or cone cell.

If $t \sim 0$, then, applying Equation 1, the maximum resolution of our setup (in diopters) is $$D_{min} = 2000 \max\left(\frac{p_d}{fa}, \frac{p_e}{f_e a}\right) \quad \text{(Equation 2)}$$

where a is the spacing (pitch) between pinholes or used lenslets, f is the distance between the display plane and the pinhole or lenslet plane, $p_e$ is the "pixel size"—equivalent at the retina, $f_e$ is the eye's focal length, and $p_d$ is the pixel size of the display (and is equal to the smallest shift c).

For example, with a pin-hole spacing, a=3 mm, this comes to 0.15 diopters as the upper bound set by $p_c$. This is further reduced by diffraction in the eye and the optics of this invention.

Figure 7:
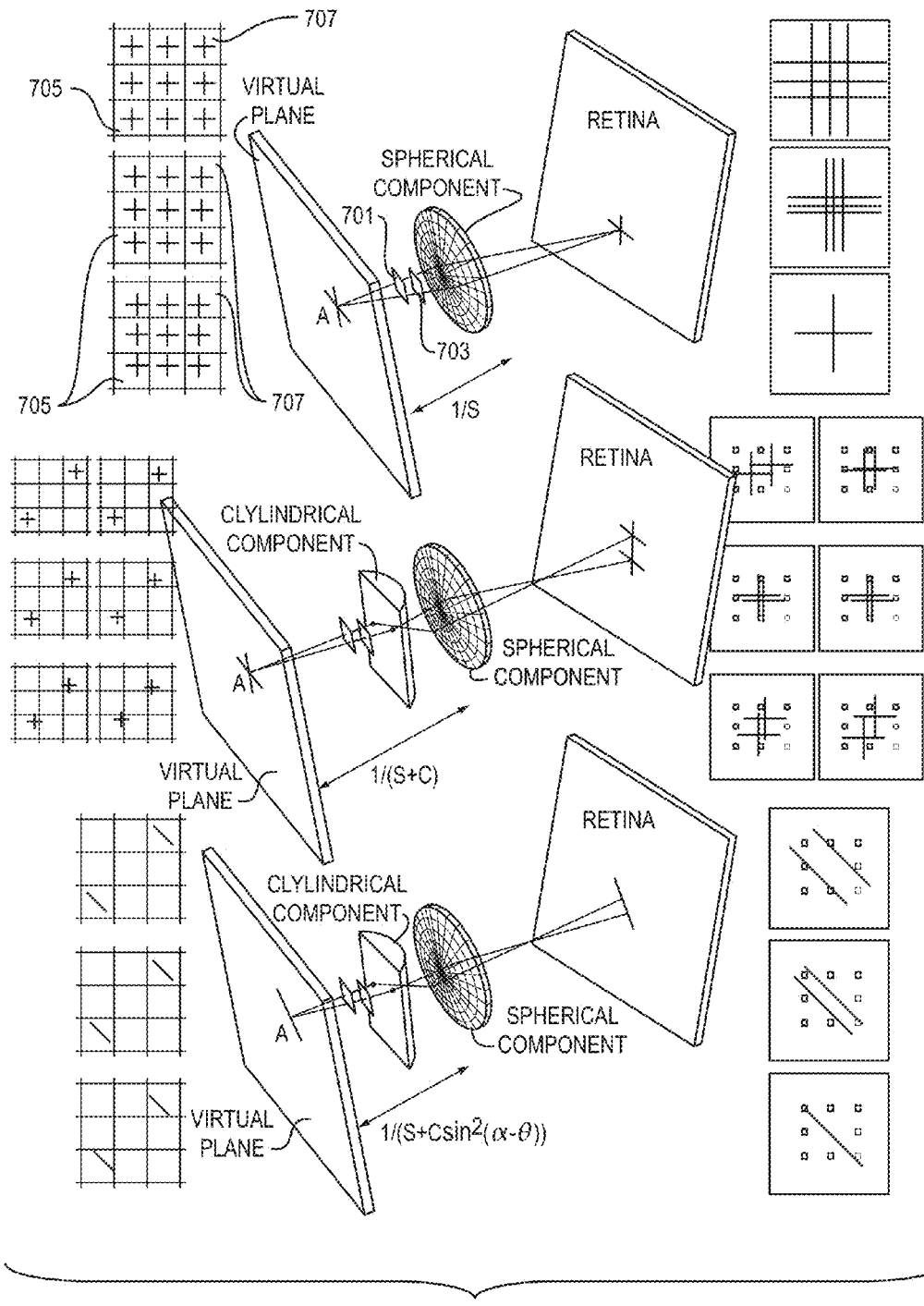
FIG. 7 is a diagram showing images displayed at the display plane and images seen by a user, in various scenarios.

In exemplary implementations of this invention, myopia may be easily measured. For example, consider an implementation that uses a microlens array. The viewer looks through the microlens array and sees multiple partially overlapping patterns (one from each lenslet, as shown in FIG. 7, top). The viewer proceeds with a 1D search and tries to align the patterns by shifting them under the lenslets (either moving them closer or moving them apart). The spacing between the patterns (on the LCD) when they appear aligned (as seen by the user through the lenslets) gives a measure of myopia. Throughout this process, the viewer's eye is focused as close to infinity as it can get (completely relaxed state) due to the bundle of parallel rays arriving from each lenslet.

For measuring hyperopia, the virtual point is moved away from the eye causing the eye to accommodate until the lens is completely relaxed, but the image is still sharply focused. Moving the virtual point any farther results in multiple overlapping images. The distance at which the eye is no longer able to focus on the pattern gives a measure of the degree of hyperopia.

The simplified ray diagrams shown in FIGS. 3 and 4 work well with spherical lens (and assessing radially symmetric disorders such as myopia and hyperopia), but are inadequate to describe non-radially symmetric or higher-order aberrations.

Astigmatism is a common refractive error due to irregular shape of the cornea and/or the eye lens. It causes the eye to refract light in a radially asymmetric manner. Astigmatism cannot be corrected with only a spherical lens. Moving a virtual point in a radially symmetric manner does not lead to a correct assessment of astigmatism.

For astigmatism, we need to look at how the generalized ray-space is transformed outside and inside the eye. An astigmatic eye is often modeled as a toric (sphero-cylindrical) patch, and its refractive power $P(\theta)$ along a meridian with direction θ is characterized as $$P(\theta)=S+C\sin^2(\alpha-\theta)$$

where S is the eye's spherical power, C is its cylindrical power, and α is the angle of the cylinder axis. It follows that $\min(P(\theta))=S$, and $\max(P(\theta))=S+C$.

Unfortunately aligning most patterns (such as a cross) is not easy in presence of astigmatism due to cylindrical aberrations (as shown in FIG. 7, middle). Unlike the spherical case, moving two dots along the radial direction produces a spiral in their observed positions, and they may never overlap. A single virtual point maps to two different image points. Lines aligned with the cylindrical axis (vertical axis in FIG. 7) are collinear but lines at any other orientation do not become collinear. Since the astigmatism axis is not known a-priori, it is challenging to design patterns and their movement for optimal alignment strategies. Allowing 2D perturbations to align two points works but the process is slow, tedious, and error prone (2D search).

In exemplary implementations of this invention, this problems is solved by exposing two lenslets at a time oriented at angle θ (as shown in FIG. 7, bottom). We notice that only a line segment placed at orientation $(\theta+\pi/2)$ will become collinear when the virtual image is created in the front focal plane at a distance $1/(S+C\sin^2(\alpha-\theta))$ from the lens. The diopter at this meridian is calculated by computing the number of steps required while moving these two parallel line segments perpendicular to each other. Note: for an astigmatic eye: (1) all line segment orientations, other than $(\theta+\pi/2)$ may lead to incorrect results, and (2) all distances (other than $1/(S+C\sin^2(\alpha-\theta))$ may lead to incorrect results.

By evaluating the eye's refractive errors along $\theta \in [0,\pi)$, the values for the eye's S, C, and α parameters can be determined. A small number of such measurements are collected along different meridians, and used to find an optimal (in the least squares sense) estimate of the eye's parameters. The meridians that are sampled may be equally spaced, but such equal spacing is not necessary.

FIG. 7 illustrates alignment challenges in the context of astigmatism, and how these challenges are solved. FIG. 7 shows three cases: (1) (Top) Where the eye has only a spherical aberration, and no astigmatism, the user can align cross-shaped patterns: (2) (Middle) Where the eye has astigmatism, the user cannot align two cross shapes, and (3) (Bottom) Where the eye has astigmatism, the user is able to align two straight line segments, if they are oriented at $(\theta + \pi/2)$.

For each case (Top, Bottom, Middle) illustrated in FIG. 7, the images on the left show patterns displayed on the screen. Each cell of a grid represents the display under a pinhole/lenslet. The images on the right show what the user would see. FIG. 7 shows what happens when the user moves the patterns closer to each other. For each case, there is a sequence of three grids of cross-shaped images on the left, showing (from top to bottom) the displayed shapes moving closer together, and a sequence of three photos on right, showing (from top to bottom) how the images seen by the user become more aligned. Each sequence of photographs on the right was taken by a camera with simulated myopia.

The case shown in the top portion of FIG. 7 is an eye with only spherical aberrations. In that case, the spherical power S may be measured by displaying a cross pattern (or any other pattern) under two lenslets (e.g. lenslet 701 and lenslet 703 which are over the upper right cell 705 and bottom left cell 707 of the grid, respectively). The user then moves the patterns until they align on the retina. This alignment happens when the virtual cross A is at distance 1/S from the lens.

The cases shown in the middle and bottom portions of FIG. 7 are for an astigmatic eye, i.e., an eye with cylindrical aberrations.

The middle case in FIG. 7 shows the difficulties that may arise in trying to align a general shape, such as a cross, in the presence of an astigmatic aberration. Unfortunately, the creation of virtual points in the focal plane of the sphero-cylindrical lens at 1/(S+C) does not assist with alignment in presence of cylindrical aberrations. Unlike the spherical case, the cross sign centers do not necessarily meet if we simply move them toward or away from the center.

The bottom case in FIG. 7 shows a solution to this problem, in exemplary implementations of this invention. The solution involves moving line segments oriented perpendicular to the line joining the two lenslets (i.e., oriented at $(\theta + \pi/2)$. The spacing at which these lines are perceived by the user as overlapping gives the power along the corresponding meridian, as discussed above. In the example shown at the bottom of FIG. 7, the cylinder is oriented so that $\alpha$ equals 90 degrees. Thus, in that particular example, the formula reduces to $1/(S+C \sin^2\theta)$.

For measuring accommodation range, in addition to testing the far focusing distance, we also test the close focusing distance by moving the virtual point closer until the eye stops focusing on it. This also gives a measure of presbyopia (bad near sight due to old age), where the lens has a reduced accommodation range.

In exemplary implementations of this invention, a two step process is employed. First, astigmatism is measured, yielding estimates of the spherical power, cylindrical power and cylindrical axis of the eye, as described above. Second, symmetric accommodation patterns are projected along the cylindrical axis for testing accommodation range.

FIGS. 8A through 8E shows some of the different visual patterns that were tested in a prototype of this invention. For each of these Figures, the top portion shows a pair of shapes used for alignment, and the bottom portion shows the pattern obtained after the shapes are aligned.

In exemplary implementations of this invention with a lenslet array, two distinct focus cues are provide for the viewer—one at infinity (due to the fact that the light exiting each lenslet, respectively, is collimated) and another at a finite depth (due to overlap among the different lenslet views, the position of the virtual object). One focus cue may be strengthened over another, depending on the patterns displayed under each lenslet. The ability to switch between the two provides greater flexibility in measuring refractive errors and accommodation range.

In conventional assessment methods, a distant scene or cycloplegic eye drops are used to keep the eye focused at infinity (i.e., to discourage accommodation).

In contrast, in exemplary implementations of this invention with a lenslet array, when it is desirable to keep the eye focused at infinity (i.e., to discourage accommodation), the bundle of parallel rays coming from each lenslet is used to fix eye focus at (for a perfect eye) or close to (for a myopic eye) infinity. Also, two extreme lenslets are used to produce a disjoint blur and discourage accommodation. (Examples of "extreme lenslets" in a 3×3 grid would be the upper right and bottom left lenslets, or the right middle and left middle lenslets.) Straight line segments, such as those shown in FIG. 8A, are helpful for measuring astigmatism, because they do not overpower the focus cue provided by the parallel rays.

In exemplary implementations of this invention, when it is desirable to keep the eye focused at the virtual point, a smooth sinusoidal pattern may be used, such as shown in FIGS. 8B and 8D. To encourage accommodation (so that the eye focuses on the virtual point), identical patterns may be used under the lenslets.

Identical, sinusoidal patterns (such as those shown in FIG. 8D) are useful for measuring accommodation range and speed, and presbyopia. For example, in a test of accommodation range, the 1D sinusoid shown in FIG. 8D may be symmetrically projected along the axis of the cylindrical power.

Alternately, hybrid patterns may allow for both accommodation and alignment. Smooth transitions in the pattern encourage accommodation, while sharp parts allow the user to easily judge when the images are misaligned, or out of focus. An example is a combination of the sinusoidal pattern with the line pattern. This pattern may be used to test whether the user is focusing at infinity, and for measuring accommodation range. The sinusoidal pattern is displayed under several lenslets, and the lines are displayed only under the extreme lenslets; the lines overlap when the image is in focus, and split when the patterns misalign.

In some implementations, a regular array of pinholes may be used, rather than a lenslet array. The pinholes have less light throughput than a lenslet array. To compensate, a brighter display may be employed.

If a lenslet array is used, crosstalk between the ray bundles exiting from the respective lenslets may be reduced by skipping every other lenslet.

Figure 9B:
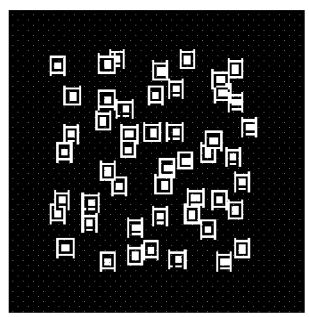
FIG. 9B shows a correspondingly jittered display mask pattern.
Figure 9D:
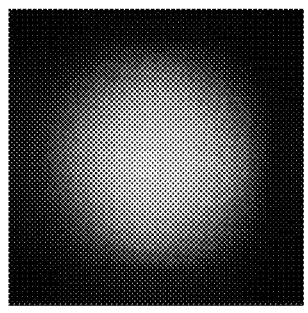
FIG. 9D shows that the shape does not stand out clearly against a blurred background, when the virtual point is not within the eye's range of accommodation.
Figure 9A:
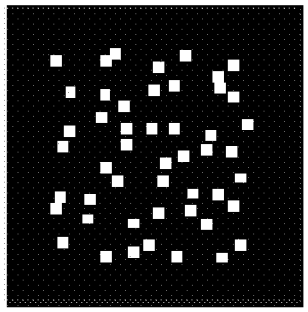
FIG. 9A shows a jittered pinhole pattern.

If pinholes are used, crosstalk between the ray bundles from the respective pinholes is also a problem. To solve that problem, the constraint of regularly spaced pinholes may be relaxed. Instead, each pinhole may be jittered by a small amount (as shown in FIG. 9A). Also the pattern behind each pinhole in the display mask or LCD may be correspondingly jittered (as shown in FIG. 9B). The jittered pattern converts the crosstalk between pinholes into random noise. This is useful when pinhole spacing is small (more light throughput) or mask to pinhole distance is large (increased power resolution) and structured crosstalk may confuse the viewer. Due to the irregular arrangement, these patterns are harder to use with microlens arrays.

Given a desired pattern, g, and a jittered pin-hole array, h, placed at distance f from pattern p, the pattern p may be obtained by convolution, p=h$\hat{x}$g. The eye when focused at infinity integrates all the parallel rays into a single spot, and the parallel ray intensity in angular direction β is given by h(x)p(x−fβ). Thus, the formed eye image is given by $$I(\beta) = \sum_x (h(x)p(x-f\beta)) = h \star p,$$

where ★ implies cross-correlation. Thus, I=h★h$\hat{x}$g. It is clear that to present image g to a human eye, we must use a jittered pinhole pattern h, whose autocorrelation is a delta function. This means h should be a pin-hole (the trivial solution) or a pseudorandom pattern with a broadband frequency response. h is created by jittering pin-holes from their uniform grid positions. The printed pattern is a convolution of a signal S convolved with the pin-hole array pattern P. When the eye sees through the pin-hole array, P, it performs a deconvolution to get S back. This indicates the constraints on P. It should not be frequency suppressing; instead, it should be broadband.

Figure 9C:
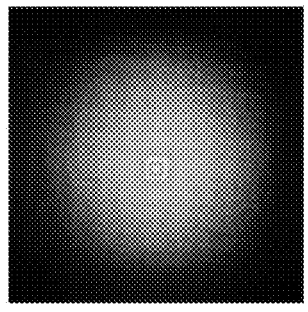
FIG. 9C shows a shape standing out clearly against a blurred background, when the virtual point is within the eye's range of accommodation.

FIG. 9A shows a jittered pinhole pattern (h). FIG. 9B shows a corresponding display mask (p) for 0 diopters. When viewing this jittered pinhole setup, a perfect eye sees a distinct pattern (g) in the middle (as shown in FIG. 9C), while a myopic eye sees a blurred image (as shown in FIG. 9D). By scaling g, one can move the virtual point closer to the lenslet of moving far away from it.

The LCD display screen may be housed in a variety of different form factors. For example, it may comprise a display screen of a cell phone, smart phone, or head mounted display (HMD). Or, for example, the LCD display screen may comprise a computer monitor. In that case, relay optics may be used to create, at the focal plane of the lenslet array, a minified display of the image on the computer monitor. This system does not require LCDs. Any kind of electronic visual display, including DMDs-based, DLPs-based, OLED, Plasma, or CRT displays, may be used.

Figure 10A:
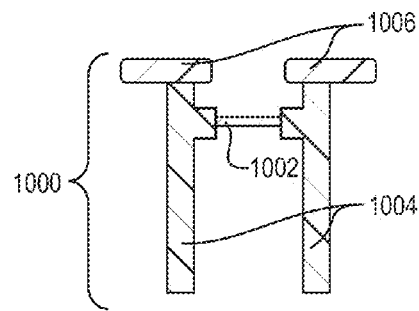
FIG. 10A shows a device with a lenslet array that may be held up to an LCD screen of a smartphone.

The lenslet or pinhole array may be affixed over the display screen. Alternately, the lenslet or pinhole array may be housed in a separate, handheld tool that is held up to the display screen. FIG. 10A is a cross-sectional view of such a handheld device 1000, in an exemplary implementation of this invention. A lenslet or pinhole array 1002 is housed in a rigid housing 1004. The user holds the eye to be tested up to an eyecup 1006. In another version, the LCD may be inside the pinhole attachment, making it a complete package for measuring refractive errors, without the need to be a snap-on for another display.

Figure 10B:
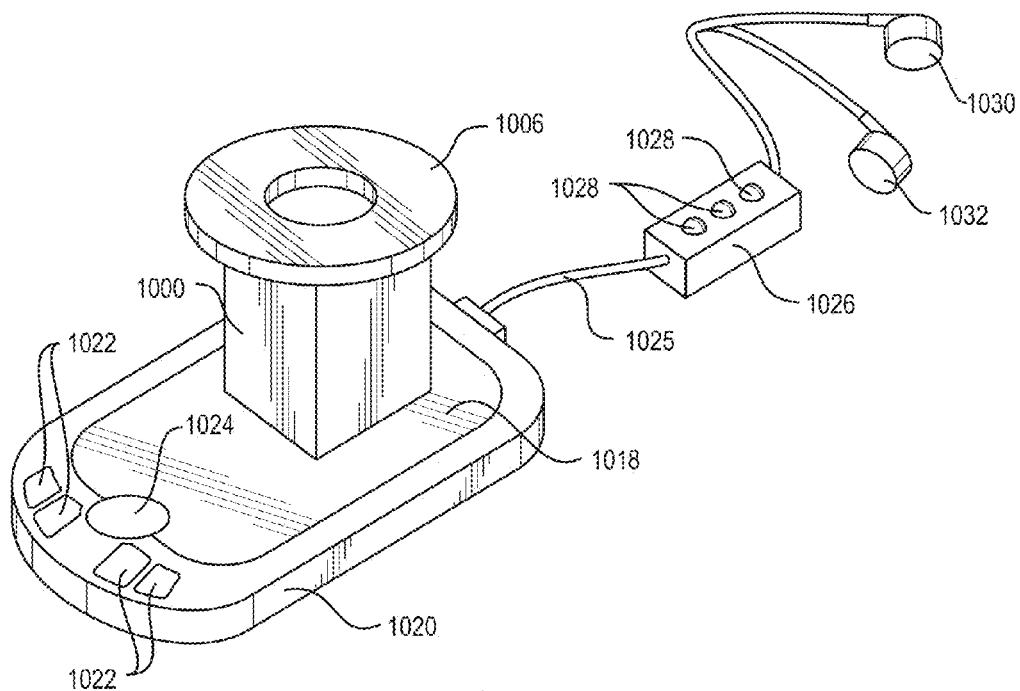
FIG. 10B shows such a device positioned adjacent to a smartphone.

FIG. 10B shows the handheld device 1000 as it is held up to the display screen 1018 of a cell phone 1020. Cell phone buttons 1022, 1024, 1028 are employed by a user to control interactive software. This software allows the user to, among other things, align the displayed images and input indications of the user's subjective experience (such as that the user sees an aligned image). Earphones 1030, 1032 may be employed by a user to hear audio instructions, such as instructions about how to take the visual acuity test. A small input device 1026 houses volume, play and pause buttons 1028 for controlling the audio output. A cable 1025 connects the input device 1026 and the cell phone 1020.

Figure 10C:
FIG. 10C shows a processor inside such a smartphone.

FIG. 10C shows a processor 1021 in the cell phone 1020. Such a processor may be used for running software for (among other things) accepting user input, controlling the display of test images on the screen, interaction via a graphical user interface, and calculating eye parameters. Alternately, more than one processor may be used, and all or some of such processors may be housed separately from the display screen, including at remote locations. Remotely located processors may be connected to each other or the LCD display device, by either wired or wireless connections.

In some embodiments of this invention, images are displayed by masks or slides, rather than a dynamic LCD screen. In that case, to change frames, a set of different masks or slides may be transposed relative to the lenslet or pinhole array, so that a different one of the masks or slides is illuminated. This process may be repeated so that a sequence of different masks or slides is displayed. A wide variety of materials may be used for the slides or masks. For example, in a prototype of this invention, a display mask comprises a transparency film, a portion of which is painted black by a laser printer.

Figure 11A:
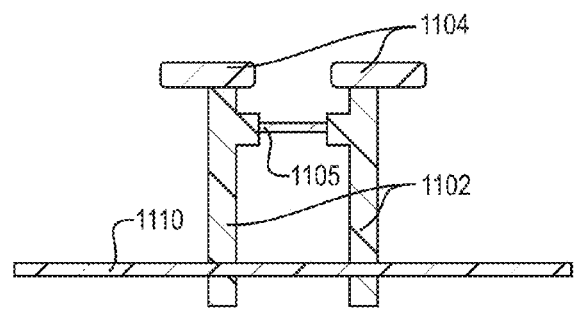
FIG. 11A, 11B, and 11C are diagrams that show cross-sectional, perspective and top views (respectively) of a device that houses a pinhole array and includes a moveable set of display masks.
Figure 11B:
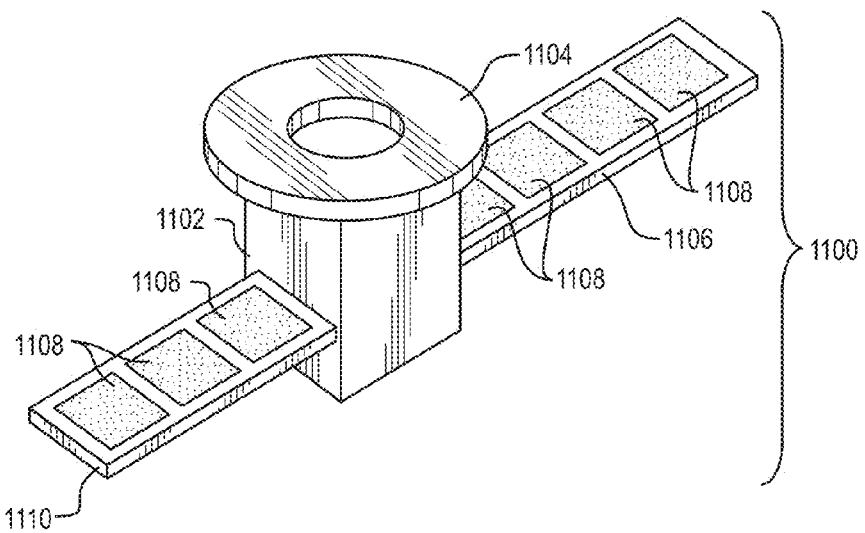
Figure 11C:
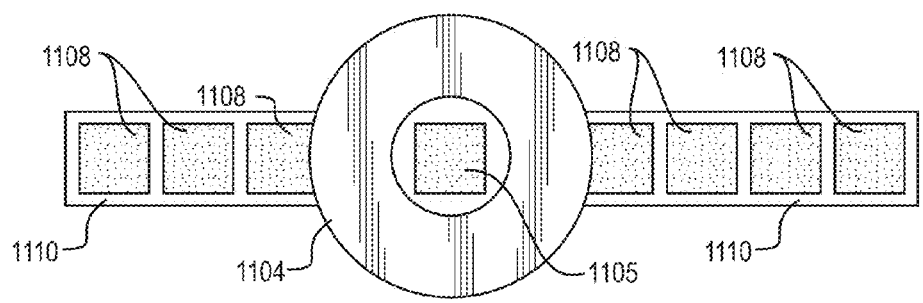

FIGS. 11A, 11B and 11C are cross-sectional, perspective and top views, respectively, of a setup in which the display can be changed by translating masks under a pinhole array, in an exemplary implementation of this invention. In these Figures, a handheld device 1100 with rigid walls 1102 houses a pinhole array 1105. A user can put his eye against the eyepiece 1104. A set of display masks 1108 is located in a moveable arm 1110. To change the frame the user can manually slide the moveable arm 1110, until a new mask is displayed. When being tested for visual acuity, a user may slide the moveable arm to the point where an image appears. At that point, the user may look at the bottom of the device to see a printed value in diopters. For example, each image may be 0.5 diopters greater or lesser than the previous. The mask may be illuminated by ambient light, or by any other light source, such as an LED, flashlight or light bulb.

A problem with pinholes is that the eye's focus tends to float. To solve this problem, when it is desirable that the eye being tested should focus at infinity, the user may be instructed to look at a distant scene with the other eye.

Another way to solve this problem (of the focal distance of the eye floating when pinholes are employed), is to use a beamsplitter to display two images at the same time to the eye being tested. One image is a background image, the other is a test image (which is projected into a black circle in the middle of the background image). The eye tends to focus at the apparent distance of the background image, at the same time that it sees the test image.

Figure 12:
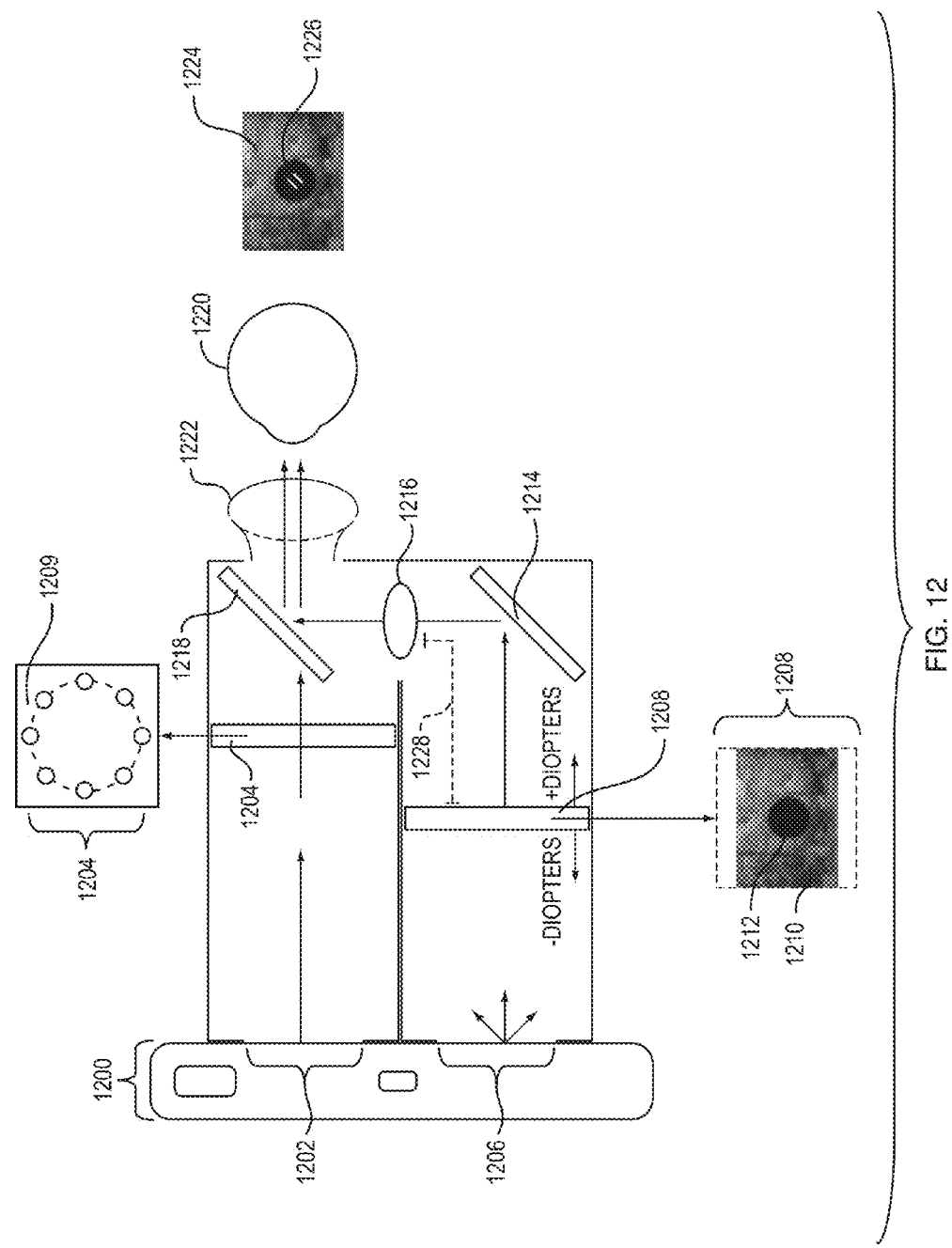
FIG. 12 is a diagram of a beam splitter device that displays both a background image and a test image at the same time, in order to force the eye to focus at the apparent distance of the background image while its refractive power is assessed.

FIG. 12 illustrates the use of a beamsplitter, in an exemplary implementation of this invention. Part of an LCD screen of a cellphone 1200 displays testing patterns 1202. Light from these testing patterns 1202 passes through a pinhole array 1204, which comprises eight pinholes 1209 equally spaced around a circle. Another part of the LCD screen on the cellphone displays a brightness adjustable uniform square 1206. Light from this illuminated square backlights a moveable background image 1208. This background image has two parts. The larger part 1210 may, for example, be a photo of forest. The smaller part, 1212, is a black hole into which the test image will be projected. Light from the moveable background image 1208 travels to the user's eye 1220 by bouncing off a front-face mirror 1214, passing through a lens 1216, and bouncing off a beamsplitter 1218. Light from the pinhole array 1204 passes through the beamsplitter 1218 and then reaches the subject's eye 1220. The user may hold his eye 1220 up to an eyecup 1222. The user will see an image 1226, comprising both the background image 1224 and a black circle with test image inside it 1226.

In this example, the eye tends to focus at the apparent depth of the background image 1224. The default distance from the lens 1228 to the moveable background image 1208 is equal to the focal length 1228 of the lens 1216. At this distance, the image will be projected at infinity. The user can manually adjust the physical position of the moveable background image 1208, in steps of say 1 diopter. The movement of the background image 1208 can simulate the range of say +6 to −3 diopters.

The background image is used to force the eye to focus at a particular distance. While the eye is so focused, the user can align patterns in the test image (that the user sees in the black inner circle 1226) to order to measure lens aberration.

FIG. 13 shows the use of a head mounted display 1300 (HMD), in an exemplary implementation of this invention. In FIG. 13, lenslet or pinhole arrays 1309 and 1311 (housed in frames 1305, 1307 are placed over the LCD displays of the HMD (which LCD displays are located within housing 1301, 1303).

Alternately, the LCD display screen may comprise a computer monitor. In any case, relay optics may be used to create, at the focal plane of a lenslet array, a minified display of the image on the computer monitor. FIG. 14A shows an example of such a set-up. The screen of a computer monitor 1302 displays test patterns. Relay optics 1304 are used to create a minified display of these test patterns, at the focal plane of the lenslet array. A user may view the test patterns by looking into an eyepiece 1306. A user may input instructions, and interact with a graphical user interface on the monitor 1302, by using a mouse 1310 or keyboard 1312. A processor in a computer 1308 may be used for, among other things, executing software instructions for (among other things) accepting user input, controlling the display of test images on the monitor screen, interacting with a user via a graphical user interface, and calculating eye parameters. Alternately, one or more processors may perform these functions, and at least some of these processors may be housed separately, including at remote locations such as a web server. Remotely located processors may be connected to each other or the electronic visual display, by either wired or wireless connections.

Figure 14B:
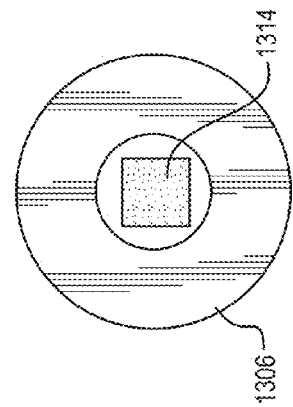
FIG. 14B is a top view of a lenslet array and relay optics.
Figure 14A:
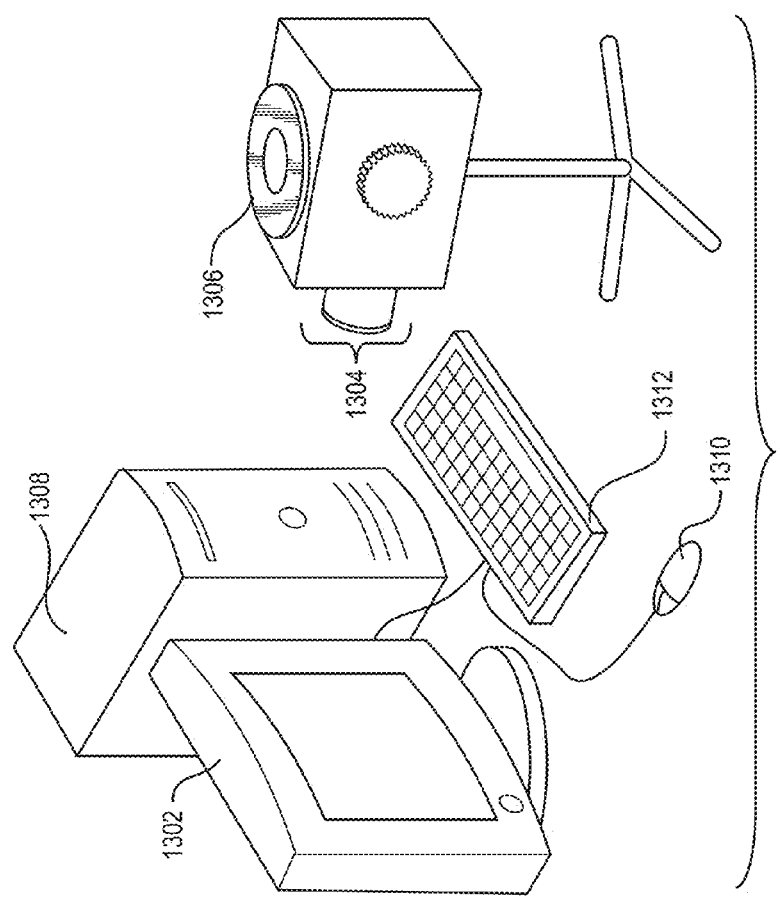
FIGS. 14A is a diagram showing relay optics for creating, on the focal plane of a lenslet array, a minified image of the display on a computer monitor.

FIG. 14B shows a top view of the relay optics. A user may place his eye against an eyecup 1306, in order to look into a lenslet or pinhole array 1314.

FIG. 15 is a diagram that shows examples of input devices that may be used, in exemplary implementations of this invention. For example, a user may employ a keyboard 1403, mouse 1405, button 1407, dial 1409, or cell phone key 1411 in order to input instructions or other data to a computer processor 1401. The processor 1401 may accept such input. In accordance with this input, the processor 1401 may, among other things, control an electronic visual display 1402 (such as an LCD) to cause the apparent positions of the displayed patterns, as seen by the eye, to move closer together or farther apart. Or, if the inputted data indicates that the displayed patterns appear to be aligned, the processor may, based on that input, determine at least one refractive parameter of the eye being tested.

Depending on the implementation, input may come from a variety of sources. In some implementations of this invention, instructions or data are inputted by a human other than the person whose eye is being tested. Alternately, input may come from a computer. For example, input from the human whose eye is being tested, or from another human, or from a computer, may be used for varying patterns (as seen by the eye or other optical system being tested). Likewise, such input may be used for indicating that patterns (as seen by the eye or other optical system being tested) appear to form a desired image.

In one of the prototypes of this invention, a set-up similar to that shown in FIGS. 14A and 14B is employed. This prototype uses a 24" Dell® 2407WFP LCD display (1920×1200 pixels) coupled with an optical minification system (factor of 1/35.8), and an array of 20×20 500-microns lenslets with focal length 12.5 mm (Edmund Optics® part number NT64-479). The minification system creates a virtual display of 3,320 DPI on the focal plane of the micro lenses, which is equivalent to a 7.5μm pixel-pitch display. As per Equation 1, we have a=3.5 mm , and c=0.0075× number of displaced pixels. An eyepiece guarantees that t=15 mm , giving approximately ±0.16 diopters per displaced pixel on the LCD. As per Equation 2, this setup is close to being limited by size of the cone cells in the eye.

In other prototypes of this invention, other high-resolution screens were used that varied in size, interface, and screen resolution (pixels per inch). In a cell phone setup, we used a Samsung® Behold I, which has a display with 180 DPI (or 540 DPI with three color channels in 1D), and a Google® Nexus® One phone, which has a display with 250 DPI (or 750 DPI with three color channels in 1D). Using a pinhole mask with 3 mm hole pitch and a distance f=20 mm , these prototypes provide approximately 0.71 diopter and 0.4 diopter per displaced pixel, respectively. The pinhole array pattern is a regular 3×3 grid where each squared pinhole has a width of 0.5 mm. We also used a Vuzix® iWear® VR 920 head mounted display (1806 DPI) and a 500-microns lenslets with focal length 12.5 mm (Edmund Optics® part number NT64-479), which results in ±0.35 diopters per displaced pixel when a=3.5 mm.

In exemplary implementations, this invention has a time-dimension and is useful for estimating speed of accommodation. This approach is suitable to detect healthy conditions of the ciliary muscles, temporary tiredness, or intoxication. A virtual pattern is shown at some depth and in the next frame it is changed to a different depth. A young, healthy subject takes approximately 350 ms to re-accommodate. Alternately, the speed of focusing of a consumer video camera may be checked in this manner. For example, a virtual object at infinity may be shown to the camera and, in the very next frame, the virtual object may be shown at 20 cm.

Chromatic aberration in the eye and microlens may produce virtual points at different depths, making the use of colored patterns tricky. However, color patterns were used in one of our prototypes to increase the effective display resolution with reasonable success.

In exemplary implementations, this invention can be built by retrofitting an existing high resolution display, such as a mobile phone. Such retrofitting may be accomplished by simple and cheap hardware and software modifications. In such a retrofitted approach, the lenslet or pinhole array may be housed in a separate, handheld device, such as that shown in FIGS. 10A and 10B.

In exemplary implementations of this invention, estimation and verification are combined in a single step and employ an alignment task instead of a blur test. This contrasts with the most common practice in optometry today.

In exemplary implementations, the ability to project virtual patterns at different distances from the viewer allows the range and speed of accommodation to be measured.

This invention is not limited to alignment as an indication of misfocus. Instead, focus or misfocus may be indicated by any change in an image, as seen by the eye or other optical system being tested, such as: (a) a temporal or spatial variation in color, (b) movement, including movement of at least one pattern, (c) a change in shape of at least one pattern, (d) a change in relative position of patterns with respect to each other.

For clarity's sake, a few definitions:

The terms "seen" and "appear" shall be construed broadly to apply to both animate and inanimate optical systems. For example, if something can be "seen" by a camera, that means it is visible from the viewpoint of the camera. Also, for example, if something "appears" to a camera, this means that it appears from the viewpoint of the camera.

The term "desired image" shall be construed broadly to include any image that meets at least one criterion for selection of that image, regardless of whether the selection is being made by an animate or inanimate decision maker, such as a human or a computer.

The terms "over" and "under" are not limited to vertical contexts, but shall be construed broadly. For example, regardless of the orientation of the display screen, a pattern displayed on the screen is "under" a lenslet if a line normal to the screen intersects both the pattern and the lenslet. Also, for example, if a device comprises both a display screen and an adjacent array which are parallel to each other, then the array is "over" the display screen regardless of the orientation of that device.

The term "including" (and grammatical variations thereof) shall be construed broadly as if followed by the words "without limitation".

This invention may be implemented in many different ways. Here are a few examples:

This invention may be implemented as a process for assessing an optical system, said process comprising in combination: (a) controlling an electronic visual display to display patterns under at least some lenslets or pinholes in an array of lenslets or pinholes, which array is positioned so that light from the electronic visual display passes through the array and reaches the optical system, (b) controlling the electronic visual display to change the patterns, as seen by the optical system, in accordance with control input, (c) accepting input indicating that the patterns appear, to the optical system, to form a desired image, and (d) determining, based on the input regarding apparent formation of the desired image, at least one refractive parameter of the optical system.

This invention may be implemented as apparatus comprising, in combination: (a) an array of lenslets or pinholes, positioned or adapted for being positioned over an electronic visual display so that light from the electronic visual display can pass through the array and reach an optical system, and (b) at least one processor for (I) controlling the electronic visual display to display patterns under at least some lenslets or pinholes in the array, (II) controlling the electronic visual display to cause the apparent positions of the patterns, as seen by the optical system, to move closer together or farther apart, in accordance with control input, (III) accepting input indicating that the patterns appear, to the optical system, to align to form a single image, and (IV) determining, based on said input regarding apparent alignment, at least one refractive parameter of the optical system. Such apparatus may further comprise the electronic visual display.

This invention may be implemented as apparatus comprising, in combination: (a) an array of lenslets or pinholes, positioned or adapted for being positioned over an electronic visual display so that light from the electronic visual display can pass through the array and reach an optical system, and (b) at least one processor for (I) controlling the electronic visual display to display patterns under at least some lenslets or pinholes in the array, (II) controlling the electronic visual display to change the patterns, as seen by the optical system, in accordance with control input, (III) accepting input indicating that the patterns appear, to the optical system, to form a desired image, and (IV) determining, based on said input regarding apparent alignment, at least one refractive parameter of the optical system. The apparatus may also comprise at least one of (I) the electronic visual display and (2) a beamsplitter for presenting both a first image and a second image to the eye at the same time, the first image for providing a cue for the eye to focus at the apparent depth of the first image, and the second image being a test image for assessing the at least one refractive parameter while the eye is focused at that apparent distance. The at least one processor of the apparatus may comprise multiple processors, and at least one of the multiple processors may be remote from the array.

Furthermore, in some implementations of this invention, including those described in the three immediately preceding paragraphs: (1) the electronic visual display may comprise a liquid crystal display; (2) the optical system may comprise an eye of a human user; (3) the control input and the input regarding apparent formation of desired image may be from the human user; (4) the control input and the input regarding apparent formation of desired image may be from another human user; (5) the control input and the input regarding apparent formation of desired image may be from a computer; (5) the at least one refractive parameter may be the spherical power of the eye; (6) the at least one refractive parameter may be one of (i) the cylindrical power of the eye and (ii) the cylindrical axis of the eye; (7) the at least one refractive parameter may be one of (i) the short focus distance of the eye and (ii) the far focus distance of the eye; (8) the patterns may have apparent positions relative to each other, as seen by the optical system, and at least some of the apparent positions may change; (9) at least one of the patterns, as seen by the optical system, may have a shape that changes; (10) color of the patterns, as seen by the optical system, may vary spatially or temporally; (11) at least one of the patterns, as seen by the optical system, may move; (12) if the eye's refraction is radially symmetric, the patterns may appear, to the eye, to be aligned when the distance from the lenslets to a virtual object consisting of the patterns is equal to $1/S$, where S is the spherical power, in diopters, of the eye; (13) if the eye's refraction is radially asymmetric, and if the patterns displayed are only under lenslets bisected by a straight line of orientation $\theta$, and if the patterns consist of straight line segments oriented at an angle of $(\pi/2+\theta)$, then the patterns may appear, to the eye, to be aligned when the distance from the lenslets to a virtual object consisting of the patterns is equal to $1/(S+C \sin^2(\alpha-\theta))$, where S is the spherical power, in diopters, of the eye, C is the cylindrical power in diopters of the eye, and $\alpha$ is the cylindrical axis of the eye; (14) symmetric accommodation patterns may be projected along the eye's cylindrical axis, (15) the eye's range of accommodation may be determined based on the longest and shortest distances, from the lenslets to the virtual object, at which the symmetric accommodation patterns appear to the eye to be aligned, (16) the speed of accommodation of the optical system may be determined by controlling the electronic visual display to change the depth of a virtual object consisting of the patterns from one depth to a new depth, and measuring how long it takes for the optical system to accommodate to the new depth, and (17) a beamsplitter may be used to present both a first image and a second image to the eye at the same time, the first image for providing a cue for the eye to focus at the apparent depth of the first image, and the second image being a test image for assessing the at least one refractive parameter while the eye is focused at that apparent distance.

CONCLUSION

It is to be understood that the methods and apparatus which have been described above are merely illustrative applications of the principles of the invention. Numerous modifications may be made by those skilled in the art without departing from the scope of the invention. The scope of the invention is not to be limited except by the claims that follow.

What is claimed is:

1. A process for assessing an optical system, said process comprising in combination:
controlling an electronic visual display to display patterns under at least some lenslets or pinholes in an array of lenslets or pinholes, which array is positioned so that light from the electronic visual display passes through the array and reaches the optical system,
controlling the electronic visual display to change the patterns, as seen by the optical system, in accordance with control input,
accepting input indicating that the patterns appear, to the optical system, to form a desired image, and
determining, based on the input regarding apparent formation of the desired image, at least one refractive parameter of the optical system.

2. The process of claim 1, wherein the electronic visual display comprises a liquid crystal display.

3. The process of claim 1, wherein the optical system comprises an eye of a human user.

4. The process of claim 3, wherein the control input and the input regarding apparent formation of desired image are from the human user.

5. The process of claim 3, wherein the control input and the input regarding apparent formation of desired image are from another human user.

6. The process of claim 3, wherein the at least one refractive parameter is a spherical power of the eye.

7. The process of claim 3, wherein the at least one refractive parameter is one of (i) a cylindrical power of the eye and (ii) a cylindrical axis of the eye.

8. The process of claim 3, wherein the at least one refractive parameter is one of (i) a short focus distance of the eye and (ii) a far focus distance of the eye.

9. The process of claim 3, wherein:
the eye's refraction is radially symmetric; and
the patterns appear, to the eye, to be aligned when the distance from the lenslets to a virtual object consisting of the patterns is equal to $1/S$, where S is the spherical power, in diopters, of the eye.

10. The process of claim 3, wherein:
the eye's refraction is radially asymmetric;
the patterns are displayed only under lenslets bisected by a straight line of orientation $\theta$;
the patterns consist of straight line segments oriented at an angle of $(\pi/2+\theta)$; and
the patterns appear, to the eye, to be aligned when the distance from the lenslets to a virtual object consisting of the patterns is equal to $1/(S+C\sin^2(\alpha-\theta))$, where S is the spherical power, in diopters, of the eye, C is the cylindrical power in diopters of the eye, and $\alpha$ is the cylindrical axis of the eye.

11. The process of claim 10, further comprising the steps of:
projecting symmetric accommodation patterns along the eye's cylindrical axis, and
determining the eye's range of accommodation based on the longest and shortest distances, from the lenslets to the virtual object, at which the symmetric accommodation patterns appear to the eye to be aligned.

12. The process of claim 3, further comprising using a beamsplitter to present both a first image and a second image to the eye at the same time, the first image for providing a cue for the eye to focus at an apparent depth of the first image, and the second image being a test image for assessing the at least one refractive parameter while the eye is focused at that apparent depth.

13. The process of claim 1, wherein the control input and the input regarding apparent formation of desired image are from a computer.

14. The process of claim 1, wherein the patterns have apparent positions relative to each other, as seen by the optical system, and at least some of the apparent positions change.

15. The process of claim 1, wherein at least one of the patterns, as seen by the optical system, has a shape that changes.

16. The process of claim 1, wherein color of the patterns, as seen by the optical system, varies spatially or temporally.

17. The process of claim 1, wherein at least one of the patterns, as seen by the optical system, moves.

18. The process of claim 1, wherein the speed of accommodation of the optical system is determined by controlling the electronic visual display to change the depth of a virtual object consisting of the patterns from one depth to a new depth, and measuring how long it takes for the optical system to accommodate to the new depth.

19. Apparatus comprising, in combination:
an array of lenslets or pinholes, positioned or adapted for being positioned over an electronic visual display so that light from the electronic visual display can pass through the array and reach an optical system, and
at least one processor for:
controlling the electronic visual display to display patterns under at least some lenslets or pinholes in the array;
controlling the electronic visual display to cause apparent positions of the patterns, as seen by the optical system, to move closer together or farther apart, in accordance with control input;
accepting input indicating that the patterns appear, to the optical system, to align to form a single image; and
determining, based on said input regarding apparent alignment, at least one refractive parameter of the optical system.

20. The apparatus of claim 19, further comprising the electronic visual display.

21. Apparatus comprising, in combination:
an array of lenslets or pinholes, positioned or adapted for being positioned over an electronic visual display so that light from the electronic visual display can pass through the array and reach an optical system; and
at least one processor for:
controlling the electronic visual display to display patterns under at least some lenslets or pinholes in the array;
controlling the electronic visual display to change the patterns, as seen by the optical system, in accordance with control input;
accepting input indicating that the patterns appear, to the optical system, to form a desired image; and
determining, based on said input regarding apparent formation, at least one refractive parameter of the optical system.

22. The apparatus of claim 21, wherein the electronic visual display comprises a liquid crystal display.

23. The apparatus of claim 21, wherein the optical system comprises an eye of a human user.

24. The apparatus of claim 23, wherein the control input and the input regarding apparent formation of desired image are from the human user.

25. The apparatus of claim 23, wherein the control input and the input regarding apparent formation of desired image are from another human user.

26. The apparatus of claim 23, wherein the at least one refractive parameter is a spherical power of the eye.

27. The apparatus of claim 23, wherein the at least one refractive parameter is one of (i) a cylindrical power of the eye and (ii) a cylindrical axis of the eye.

28. The apparatus of claim 23, wherein the at least one refractive parameter is one of (i) a short focus distance of the eye and (ii) a far focus distance of the eye.

29. The apparatus of claim 23, wherein the at least one processor is also for performing a step comprising: controlling the electronic visual display to display the patterns so that, if the eye has radially symmetric refraction, the patterns appear to be aligned when the distance from the lenslets to a virtual object consisting of the patterns is equal to $1/S$, where S is the spherical power, in diopters, of the eye.

30. The apparatus of claim 23, wherein the at least one processor is also for performing a step comprising: controlling the electronic visual display to display the patterns as straight line segments oriented at an angle of $(\pi/2+\theta)$ that are under only lenslets bisected by a straight line of orientation $\theta$, and that appear, to the eye, to be aligned when the distance from the lenslets to a virtual object consisting of the patterns is equal to $1/(S+C \sin^2 (\alpha-\theta))$, where S is the spherical power in diopters of the eye, C is the cylindrical power in diopters of the eye, and $\alpha$ is the cylindrical axis of the eye.

31. The apparatus of claim 23, wherein the at least one processor is also for performing a step comprising: projecting symmetric accommodation patterns along the eye's cylindrical axis, and determining the eye's range of accommodation based on the longest and shortest distances, from the lenslets to a virtual object, at which the symmetric accommodation patterns appear to the eye to be aligned.

32. The apparatus of claim 23, wherein the at least one processor is also for performing a step comprising: determining the speed of accommodation of the optical system by controlling the electronic visual display to change the depth of a virtual object consisting of the patterns from one depth to a new depth, and measuring how long it takes for the optical system to accommodate to the new depth.

33. The apparatus of claim 23, further comprising a beamsplitter for presenting both a first image and a second image to the eye at the same time, the first image for providing a cue for the eye to focus at an apparent depth of the first image, and the second image being a test image for assessing the at least one refractive parameter while the eye is focused at that apparent depth.

34. The apparatus of claim 21, wherein the control input and the input regarding apparent formation of desired image are from a computer.

35. The apparatus of claim 21, wherein the patterns have apparent positions relative to each other, as seen by the optical system, and at least some of the apparent positions change.

36. The apparatus of claim 21, wherein at least one of the patterns, as seen by the optical system, has a shape that changes.

37. The apparatus of claim 21, wherein color of the patterns, as seen by the optical system, varies spatially or temporally.

38. The apparatus of claim 21, wherein at least one of the patterns, as seen by the optical system, moves.

39. The apparatus of claim 21, wherein the at least one processor comprises multiple processors, and at least one of the multiple processors is remote from the array.

* * * * *